US00PP23060P2

(12) United States Plant Patent
Korlipara

(10) Patent No.: US PP23,060 P2
(45) Date of Patent: Sep. 18, 2012

(54) ***ECHINACEA* PLANT NAMED 'SECRET LUST'**

(50) Latin Name: ***Echinacea* spp.**
Varietal Denomination: Secret Lust

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 40 days.

(21) Appl. No.: 13/066,132

(22) Filed: Apr. 6, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Secret Lust' characterized by enlarged disc florets forming an anemone-type inflorescence, soft red orange ray florets contrasting strongly with the deep red orange disc florets, a medium habit with excellent branching, strong stems, and excellent vigor.

1 Drawing Sheet

Botanical denomination: *Echinacea* spp.
Variety designation: 'Secret Lust'.

BACKGROUND OF THE INVENTION

The present invention relates to a new and distinct cultivar of *Echinacea* and given the cultivar name 'Secret Lust'. *Echinacea* is in the family *Asteraceae*. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety is shorter with more crowns, and with larger inflorescences that are orange rather than pink.

Compared to *Echinacea* 'Hot Papaya' (U.S. Plant Pat. No. 21,022), the new cultivar has more crowns, more inflorescences per stem, and an inflorescence with different orange color.

This new *Echinacea* cultivar is distinguished by:

1. enlarged disc florets forming an anemone-type inflorescence,
2. soft red orange ray florets contrasting strongly with the deep red orange disc florets,
3. a medium habit with excellent branching,
4. strong stems, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences and habit of *Echinacea* 'Secret Lust' as a one-year-old in the field in full sun in early July in Canby, Oreg.

DETAILED PLANT DESCRIPTION

The following is a detailed description of the new *Echinacea* cultivar based on observations of a two-year-old specimens growing in the trial field in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type*.—Herbaceous perennial.
*Hardiness*.—USDA Zones 4 to 9.
*Size*.—Grows to about 62 cm wide and 68 cm tall to top of inflorescences.
*Form*.—Basal clump, with about 30 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 5 to 24 flowers per stem.
*Size*.—To 66 cm tall to a terminal inflorescence and 12 mm wide at base.
*Internode length*.—1 cm to 9 cm.
*Surface texture*.—Strigose.
*Color*.—Yellow Green 144A mottled and tinted Greyed Purple 187A.

Leaf (basal):

*Type*.—Simple.
*Shape*.—Lanceolate.
*Arrangement*.—Basal.
*Blade size*.—Grows to 13 cm long and 5 cm wide.
*Margins*.—Sparsely serrate.

*Apex*.—Acute.
*Base*.—Attenuate.
*Surface texture*.—Strigose on both sides.
*Venation*.—Pinnate, with 3 main veins.
*Color*.—Topside, Green N137B, bottom side Yellow Green 147A.
*Petiole description*.—Grows to 18 cm long and 2.5 mm wide, strigose, Yellow Green 146C except at base where sometimes Greyed Purple 187A.

Leaf (stem):
*Type*.—Simple.
*Shape*.—Lanceolate.
*Arrangement*.—Alternate.
*Blade size*.—Grows to 13 cm long and 5 cm wide.
*Margins*.—Entire to sparsely serrate, somewhat undulate.
*Apex*.—Acuminate.
*Base*.—Attenuate.
*Surface texture*.—Strigose on both sides.
*Venation*.—Pinnate, with 3 main veins from the base.
*Color*.—Topside, Green N137A, bottom side closest to Yellow Green 147B.
*Petiole description*.—On lowermost leaves only, clasping, grows to 7 cm long and 5 mm wide above the clasp, glabrous, Yellow Green 146C.

Inflorescence:
*Type*.—Composite on terminal stalked heads.
*Number of flowering stems per plant*.—About 30.
*Flowering stem*.—Grows to 66 cm tall from the base of the plant to the terminal inflorescence and can grow to 20 cm long from the top stem leaf to the base of an inflorescence; branched with branches also branching, with 5 to 24 inflorescences per stem; diameter growing to 12 mm wide near the inflorescence; strigose; Yellow Green 144A mottled Greyed Purple 187A.
*Size*.—Grows to 8 cm wide and 5 cm deep as disc enlarges.
*Form*.—Ray florets held slightly reflexed, mature disc is conic.
*Immature inflorescence*.—Grows to 3.5 cm wide and 2.2 cm deep, ray florets held upright and rolled up so only the back color shows, Greyed Orange 173A, disc color Greyed Purple 187B.
*Ray florets*.—Without pistil or stamen, about 20 in number, grow to 42 mm long and 9 mm wide, oblanceolate with the tip two toothed (each acute), entire margins, base attenuate, glabrous on both sides; topside Greyed Orange 168B on the top half to Greyed Red 179A, bottom side Greyed Orange 176C.
*Disc*.—Flat becoming conic, becoming 30 mm deep and 65 mm wide with maturity, overall color is Orange Red 34A.
*Disc florets*.—About 400 in number, each with 1 pistil and 4 stamen, grow to 27 mm long and 8 mm wide, each with one persistent, very stiff linear bract (12 mm long with the top 2 mm colored Greyed Purple 187A on tip then Yellow Green 144A in middle, then White NN155D on bottom ⅓); showy 2 cleft corollas to 24 mm long and 8 mm wide, tubular on the bottom with the lobes spread out like a fan, glabrous on both sides, topside color Orange Red 34B maturing to Yellow Orange 20A with 34A on the top ⅓, back side color Yellow 20C with the top Orange Red N34A; pistil 7 to 9 mm long, ovary 2.8 mm long, White NN155D, style 4 mm long Red 54C, 2-branched stigma spreading, Greyed Purple 187A; stamen 4 mm long, anthers 1.5 mm long and Greyed Purple N186A, filaments 2.5 mm long, White 155B, very little pollen, Yellow Orange 23B.
*Phyllaries*.—In 4 leafy series, area 33 mm wide and 9 mm deep, lobes lanceolate in shape, reflexed, grow to 15 mm long and 4 mm wide, Yellow Green 147B, margins strigose, tip acute, strigose on both sides.
*Receptacle*.—Grows to 14 mm wide and 15 mm deep, White 155A.
*Bloom period*.—July through October in Canby, Oreg.
*Fragrance*.—Good, floral.
*Lastingness*.—Each inflorescence lasts about two weeks in Canby, Oreg.

Seeds: 0 to 1 per inflorescence, each 3 mm long and 2.5 mm wide, oval, Brown 200C.
*Fertility*.—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

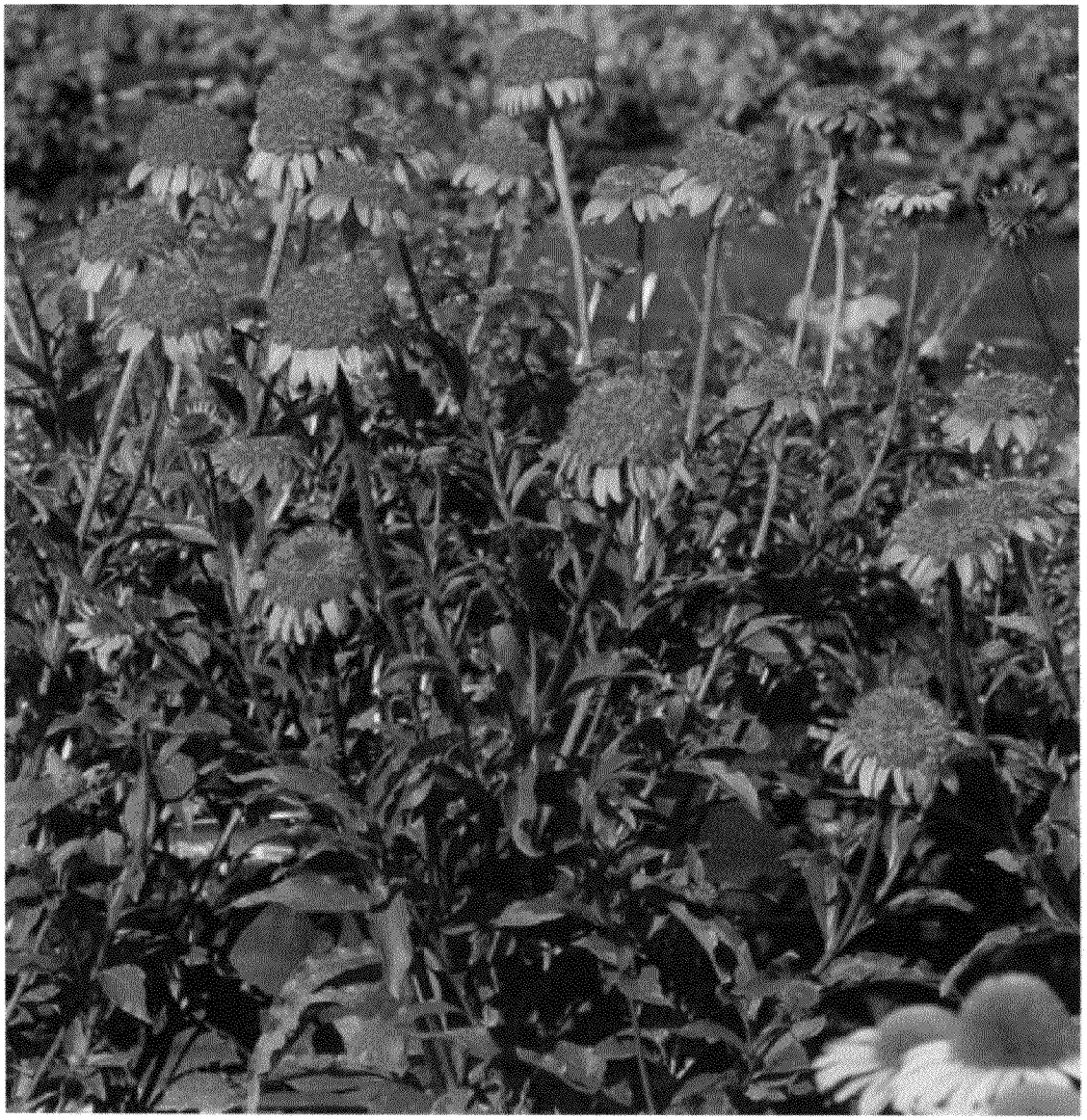

* * * * *